US00PP35550P2

(12) United States Plant Patent
Kordes

(10) Patent No.: US PP35,550 P2
(45) Date of Patent: Dec. 19, 2023

(54) FLORIBUNDA ROSE PLANT NAMED 'KORNEKCRAZ'

(50) Latin Name: *Rosa hybrida*
Varietal Denomination: KORnekcraz

(71) Applicant: W. KORDES' SÖHNE ROSENSCHULEN GMBH & CO KG, Klein Offenseth-Sparrieshoop (DE)

(72) Inventor: Wilhelm Alexander Kordes, Klein Offenseth-Sparrieshoop (DE)

(73) Assignee: W. KORDES' SÖHNE ROSENSCHULEN GMBH & CO KG, Klein Offenseth-Sparrieshoop (DE)

( * ) Notice: Subject to any disclaimer, the term of this patent is extended or adjusted under 35 U.S.C. 154(b) by 0 days.

(21) Appl. No.: 18/203,817

(22) Filed: May 31, 2023

(30) Foreign Application Priority Data

Oct. 6, 2022 (QZ) ..... PBR 2022/2229

(51) Int. Cl.
*A01H 5/02* (2018.01)
*A01H 6/74* (2018.01)

(52) U.S. Cl.
USPC ..... Plt./143

(58) Field of Classification Search
USPC ..... Plt./101, 141, 143
See application file for complete search history.

(56) References Cited

U.S. PATENT DOCUMENTS

PP10,126 P 11/1997 Carruth

*Primary Examiner* — Susan McCormick Ewoldt
(74) *Attorney, Agent, or Firm* — Panitch Schwarze Belisario & Nadel LLP; Stephany G. Small; Travis W. Bliss

(57) ABSTRACT

A new and distinct variety of Floribunda rose plant, referred to by its cultivar name, 'KORnekcraz', is described. The new variety forms in abundance on a substantially continuous basis attractive, red and white striped colored blossoms. The vegetation is vigorous, and the growth habit is very bushy. Attractive dark green, glossy foliage is formed. Additionally, the new variety is particularly well suited for growing as distinctive ornamentation in the landscape.

1 Drawing Sheet

Latin name of genus and species of plant claimed: *Rosa hybrida.*
Variety denomination: 'KORnekcraz'.

CROSS REFERENCE TO RELATED APPLICATIONS

This application claims priority to Plant Breeders' Right Application Number 2022/2229, which was filed at Community Plant Variety Office in the European Union on Oct. 6, 2022, the contents of which are hereby incorporated by reference for all purposes.

STATEMENT REGARDING PRIOR DISCLOSURES BY THE INVENTOR

The first offer for sale of the new variety was June 2022, in Germany. The first offer for sale of the new variety was by the inventor or another who obtained the new variety directly or indirectly from the inventor. No plants of the new variety have been sold in this country or anywhere in the world, nor has any disclosure of the new plant been made, more than one year prior the effective filing date of this application, and such sale or disclosure within one year was either derived directly or indirectly from the inventor.

BACKGROUND OF THE INVENTION

The new variety of floribunda rose plant of the present invention was created by controlled breeding in May 2012 at Offenseth-Sparrishoop, Germany by artificial pollination wherein two parents were crossed which previously had been studied in the hope that they would contribute the desired characteristics. The female parent (i.e., the seed parent) of the new variety was an unnamed breeder seedling (not patented). The male parent (i.e., the pollen parent) of the new variety was the 'KORblohawa' variety (not patented).

The parentage of the new variety can be summarized as follows:

Unnamed Breeder Seedling x 'KORblohawa'

The seeds resulting from the above pollination were sown and small plants were obtained which were physically and biologically different from each other. Selective study resulted in the identification of a single plant of the new variety.

The new variety has been found to undergo asexual propagation at Wasco, California and Cochranville, Pennsylvania by a number of routes such as vegetative cuttings. Asexual propagation techniques in Wasco, California and Cochranville, Pennsylvania, such as vegetative cuttings, have shown that the characteristics of the new variety are homogeneous, stable, and strictly transmissible by such asexual propagation from one generation to another. Accordingly, the new variety undergoes asexual propagation in a true-to-type manner.

SUMMARY OF THE INVENTION

It was found that the new variety of floribunda rose plant of the present invention possesses the following combination of characteristics:

(a) forms attractive, red and white striped blossoms,
(b) exhibits a very bushy growth habit,
(c) forms vigorous vegetation, and
(d) provides attractive ornamental glossy, dark green colored foliage.

The new variety well meets the needs of the horticultural industry. It can be grown to advantage as attractive ornamentation in parks, gardens, public areas, and residential landscapes. Accordingly, it is particularly well suited for growing in the landscape.

The new variety can be readily distinguished from its ancestors. More specifically, the unnamed breeding seedling female parent (i.e., the seed parent) displays a less bushy growth habit and exhibits flowers with more petals compared to the new variety. Also, the seed parent forms flowers which have pink and white colored striping, whereas the new variety forms flowers which have red and white colored striping. Additionally, the new variety provides flatter to open flower shape compared to the 'KORblohawa' variety (i.e., the pollen parent) and the flower type of the new variety is single, whereas the flower type of the 'KORblohawa' variety is double. Moreover, the new variety can be readily distinguished from non-parental related similar varieties. For example, 'Wekplapep' (U.S. Plant Pat. No. 10,126) displays more petals and exhibits more fragrance compared to the new variety.

The new variety has been named the 'KORnekcraz' variety.

BRIEF DESCRIPTION OF THE PHOTOGRAPHS

The accompanying photograph shows, as nearly true as it is reasonably possible to make the same in a color illustration of this character, typical specimens of the new variety and blossoms of the new variety. The illustrated rose plants of the new variety were approximately two years of age and were grown outdoors in a field in Ellerhoop, Germany in June 2022.

Drawing—illustrates a specimen of the plant displaying flowers at varying points of opening.

DETAILED BOTANICAL DESCRIPTION

The chart used in the identification of colors is that of The Royal Horticultural Society (The R.H.S. Colour Chart, 2015 edition). The terminology which precedes reference to the chart has been added to indicate the corresponding color in more common terms. The description is based on a two-year-old specimen of the new variety, observed during June, while growing on its own roots in a three-gallon container in a nursery in Cochranville, Pennsylvania.

Botanical classification: *Rosa hybrida* cultivar 'KORnekcraz'.

Commercial classification: Floribunda Rose.

Plant:

*Habit*.—Very bushy.

*Height*.—Approximately 60.0 cm on average from the top of the soil plane in 3-gallon pot.

*Width*.—Approximately 60.0 cm on average.

Branches:

*Stem color*.—Old wood is commonly near Yellow-Green Group 146A; young stems are commonly near Yellow-Gren Group 144A.

*Length*.—Main stems: approximately 60.0 cm on average. Secondary stems: approximately 30.0 cm on average.

*Diameter*.—Main stems: approximately 7.0 mm on average. Secondary stems: approximately 3.0 mm on average.

*Thorns*.—Amount: moderate, 3 to 6 per internode. Young thorns: length is approximately 1.5 cm on average; width is approximately 5.0 mm at point of attachment; and color is commonly near Orange-Red Group N34A. Old thorns: length is approximately 1.5 cm on average; width is approximately 5.0 mm at point of attachment; and color is commonly near Greyed-Orange Group 176A.

Leaflets:

*Number*.—3, 5, 7, and 9.

*Shape*.—Ovate; apex is acute to acuminate; and base is cuneate.

*Margin*.—Serrate.

*Undulation*.—Moderate.

*Glossiness of upper side*.—Glossy.

*Texture*.—Upper surface: smooth. Under surface: smooth.

*Size*.—Terminal leaflet: length is approximately 5.0 cm on average; width is approximately 3.0 cm on average. Lower leaflets: length is approximately 3.5 cm on average; width is approximately 2.5 cm on average. 5-Leaflet leaf: length is approximately 10.0 cm on average; width is approximately 7.5 cm on average.

Foliage:

*Young foliage*.—Upper surface color: commonly near Green Group 138A with indistinguishable venation. Under surface color: commonly near Green Group 138B with indistinguishable venation.

*Old foliage*.—Under surface color: commonly near Yellow-Green Group 147B with venation near Yellow-Green Group 144NA.

*Petiole*.—Texture: upper surface is slight hispidulous/hirsutulous; under surface is thorny. Length: approximately 2.0 cm on average. Width: approximately 1.0 mm on average. Upper surface color: commonly near Green Group 137D. Under surface color: commonly near Yellow-Green Group 144A.

*Rachis*.—Length: approximately 8.0 cm on average. Width: approximately 1.0 mm on average. Upper surface color: commonly near Green Group 137D. Under surface color: commonly near Yellow-Green Group 144A.

*Stipules*.—Length: approximately 1.0 cm on average. Width: approximately 4.0 mm on average. Margin: entire to erose. Upper surface color: commonly near Yellow-Green Group 144A. Lower surface color: commonly near Green Group 143C.

Inflorescence:

*Number of flowers*.—About 40 blooms on average on a plant at once.

*Number of blossoms per stem or in a cluster*.—Typically between 5 to 7 blooms per stem on average.

*Peduncle*.—Color: commonly near Yellow-Green Group 144A. Diameter: approximately 2.0 mm on average. Length: approximately 2.0 cm on average. Surface texture: smooth.

*Sepals*.—Number: 5. Upper surface color and texture: commonly near Yellow-Green Group 144A, covered in short pubescence. Under surface color and texture: commonly near Yellow-Green Group 148C and Green Group 143B, puberulent. Size: length is approximately 2.3 cm on average; width is approximately 6.0 mm on average. Margin: entire with extension on two or three sepals measuring 5.0 mm in length and 1.0 mm in width. Apex: acute to aristate. Base: truncate as it joins the receptacle.

*Buds*.—Shape: ovoid. Size: length is approximately 2.0 cm on average; width is approximately 1.3 cm on average. Color (when opening): commonly near Red-Purple Group 60A, Red-Purple Group 62C, Red-Purple Group 62D, and White Group N155D.

*Flower*.—Form: single, mostly flat, slightly cuplike. Profile: flat to slightly concave as it opens. Diameter: approximately 7.0 cm on average. Height: approximately 2.0 cm on average. Duration: on the plant approximately 10 to 12 days. Petal color when first and fully opened: upper surface is commonly striped with near Red Group 46B, Red Group 46A, Red-Purple Group 63C, Red-Purple Group 59A, and White Group N155B with a medium sized basal spot commonly near Greyed-Yellow Group 160A to near White Group 155A; under surface is commonly striped with near White Group N155B, Red-Purple Group 57B, and Red-Purple Group 61A with a medium sized basal spot of near White Group N155A, Red-Purple Group N57B, and Yellow Group 6A. Petal color at end of bloom: upper and under surfaces are same as when opening.

*Fragrance*.—Slight sweet scent.

*Petal*.—Number: 5 on average. Drop: good. Length: approximately 3.5 cm on average. Width: approximately 4.0 cm on average. Overall shape: broadly obovate. Margin: entire with moderate undulation. Apex shape: rounded emarginate. Base shape: cuneate.

*Petaloids*.—Not present.

*Stamen*.—Number: approximately 125. Anthers: number is approximately 125; color is commonly near Greyed-Orange Group 166B; length is approximately 1.0 mm on average; and shape is oval. Filaments: length is approximately 8.0 mm on average and color is commonly near Yellow-Orange Group 18D.

*Pistils*.—Arrangement: separate and free. Number: approximately 53. Style: length is approximately 5.0 mm and color is commonly near Yellow Group 9C. Stigma: diameter is approximately 1.0 mm on average; shape is fan shaped.

*Receptacle*.—Diameter: approximately 6.0 mm on average. Depth: approximately 6.0 mm on average. Shape: urn shaped. Color: commonly near Yellow-Green Group 144A. Surface texture: smooth.

*Pollen*.—Abundant, color is commonly near Yellow-Orange Group 20A.

*Hips/seed*.—None observed.

Development:

*Vegetation*.—Vigorous and strong.

*Blossoming*.—Abundant and substantially continuous from spring through frost; typically, in bloom outdoors from May to November in Southeastern Pennsylvania.

*Resistance to diseases*.—Good resistance for black spot, powdery mildew, and rust under normal greenhouse growing conditions in Cochranville, Pennsylvania.

*Hardiness*.—Hardy to USDA Zone 6, further hardiness testing is in process.

The new 'KORnekcraz' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of Floribunda rose plant named 'KORnekcraz' characterized by the following combination of characteristics:

(a) forms attractive, red and white striped blossoms, (b) exhibits a very bushy growth habit, (c) forms vigorous vegetation, and (d) provides attractive ornamental glossy, dark green colored foliage;

substantially as herein shown and described.

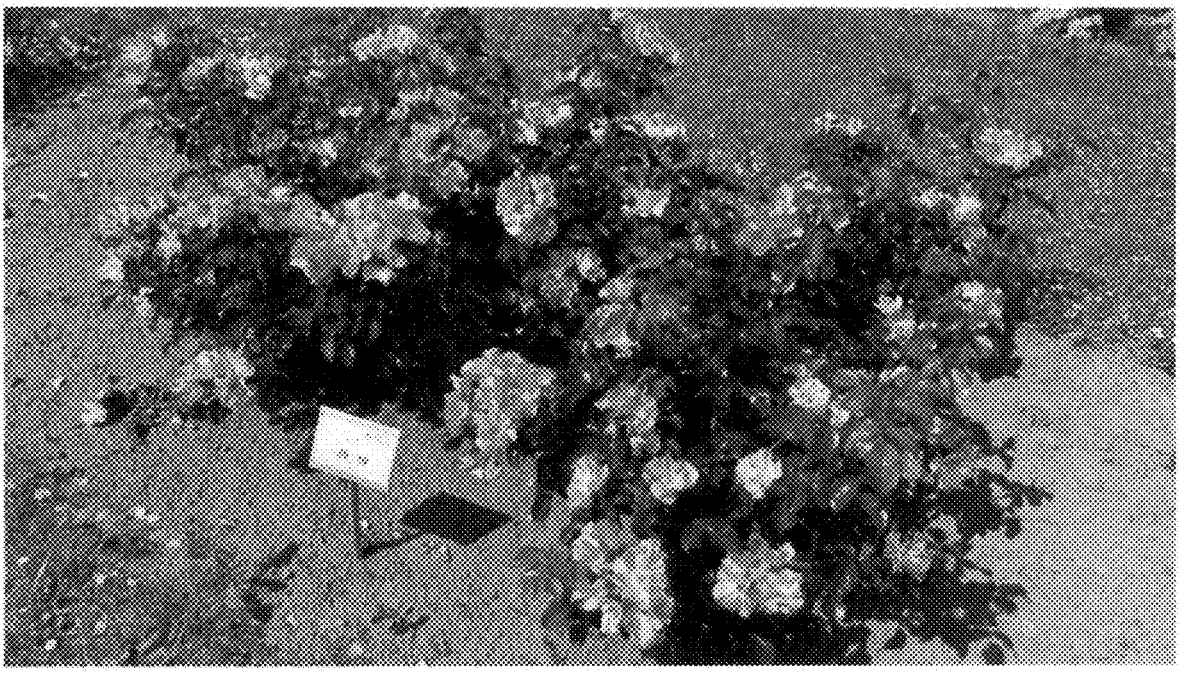

* * * * *